United States Patent [19]

Tabushi et al.

[11] 4,390,740

[45] Jun. 28, 1983

[54] PROCESS FOR PREPARING FLUOROBENZENE

[75] Inventors: Iwao Tabushi, Kyoto; Kazuhiro Shimokawa, Yame; Daiji Naito, Ibaraki; Susumu Misaki, Mino; Tsutomu Yoshida, Settsu, all of Japan

[73] Assignee: Daikin Kogyo Co., Ltd., Osaka, Japan

[21] Appl. No.: 329,434

[22] Filed: Dec. 10, 1981

[30] Foreign Application Priority Data

Dec. 13, 1980 [JP] Japan .................................. 55-176132
Dec. 28, 1980 [JP] Japan .................................. 55-186638

[51] Int. Cl.³ ............................................ C07C 17/10
[52] U.S. Cl. .................................................... 570/146
[58] Field of Search ........................................ 570/146

[56] References Cited

U.S. PATENT DOCUMENTS 3,499,942  3/1970  Nefedov et al. .................... 570/146

*Primary Examiner*—Charles F. Warren
*Assistant Examiner*—Joseph A. Boska
*Attorney, Agent, or Firm*—Birch, Stewart, Kolasch & Birch

[57] ABSTRACT

Monofluorobenzene is prepared in a good yield by reacting cyclopentadiene or its dimer of the formula:

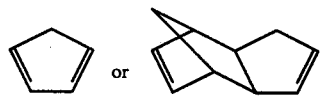

with fluorohalomethane of the formula:

$CHFX_2$ wherein Xs are, same or different, halogen atoms in the presence of a phase transfer catalyst and an acid acceptor.

4 Claims, No Drawings

PROCESS FOR PREPARING FLUOROBENZENE

This invention relates to a process for preparing fluorobenzene. More particularly, it relates to a process for preparing fluorobenzenes by reacting cyclopentadiene or its dimer, bicyclopentadiene, with fluorohalomethane.

Fluorobenzene is a very useful compound as a starting material in preparation of medicines, agricultural chemicals, dyes, etc.

For preparation of fluorobenzene or its derivatives, there are known a process including the Schiemann reaction comprising diazotizating aniline with sodium nitrite in borofluoric acid or hydrofluoric acid and pyrolyzing the obtained diazonium salt, a halogen-exchange process comprising substituting the chlorine atom of chlorobenzene having an electron attracting group at the o-position or the p-position with the fluorine atom of alkali metal fluoride in an aprotic polar solvent, a direct fluorination process comprising fluorinating benzene with fluorine gas diluted with an inert gas, etc. These processes, however, have such disadvantages as requiring expensive raw materials as well as long reaction steps and giving fluorobenzene or its derivatives only in very low yields. Further, the Schiemann reaction process includes treatment of the unstable diazonium salt, and the direct fluorination process needs to handle fluorine gas, which is very dangerous, and produces a large quantity of by-products. Thus, these processes are unsatisfactory for commercial scale production of fluorobenzene or its derivatives.

Recently, there is developed a process for preparing fluorobenzene comprising pyrolyzing cyclopentadiene or bicyclopentadiene together with fluorohalomethane at a temperature between 300° C. and 800° C. to give fluorobenzene (cf. U.K. Pat. No. 1,130,263). This process has some defects such that the reaction is carried out at a very high temperature to produce rather much by-products and requires a special equipment when being applied to commercial scale production.

As a result of the extensive study to overcome these defects of the process of said U.K. Patent, it has now been found that when the reaction is carried out in the presence of a phase transfer catalyst and an acid-acceptor, it is possible to lower the reaction temperature and to obtain the desired product in a good yield.

According to the present invention, there is provided a process for preparing monofluorobenzene which comprises reacting cyclopentadiene or its dimer of the formula:

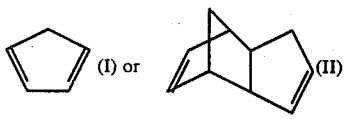

with fluorohalomethane of the formula:

CHFX$_2$      (III)

wherein Xs are same or different halogen in the presence of a phase transfer catalyst and an acid acceptor.

The reaction of the present invention may proceed according to the following reaction formula:

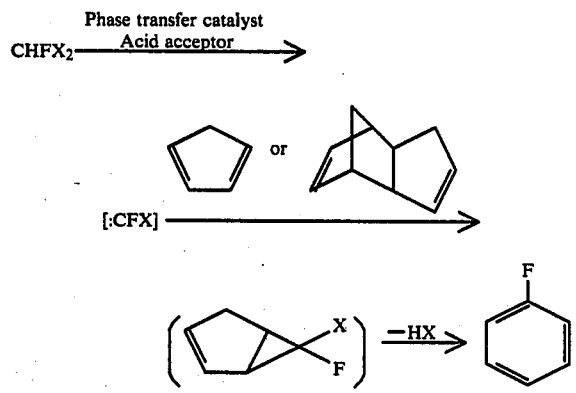

The intermediate, 6-halogeno-6-fluorobicyclo-[3.1.0]hexan-2-ene, is an unstable compound and can be converted to fluorobenzene without isolation under the present reaction condition.

Specific examples of the fluorohalomethane (III) are dichlorofluoromethane, chlorodifluoromethane, dibromofluoromethane, iododifluoromethane, trifluoromethane, etc.

Specific examples of the phase transfer catalyst to be used in the present invention are quarternary ammonium compounds, quarternary phosphonium compounds, crown ethers, cryptates and sulfonium compounds. In view of efficiency and economy, quarternary ammonium compounds are most preferable.

Preferable quarternary ammonium compounds may be represented by the formula:

$$[R_4N^+]Y^- \qquad (IV)$$

wherein Rs are same or different alkyl groups or aryl groups, preferably $C_1$–$C_{10}$ alkyl groups or $C_6$–$C_9$ aryl groups; Y is an anion selected from the group consisting of halide ion, hydroxide ion, hydrogensulphate ion, hydrogencarbonate ion, dihydrogen phosphate ion and nitrate ion. Examples of the quarternary ammonium compounds are tetramethylammonium chloride, tetraethylammonium bromide, trimethylbenzylammonium chloride, triethylbenzylammonium chloride, tetrabutylammonium bromide, tetrabutylammonium hydrogensulfate, trioctylmethylammonium chloride, etc.

As the acid acceptor, alkylene oxides, particularly $C_2$–$C_8$ alkylene oxide, alkali metal hyroxides, alkali metal alcoholates, particularly alkali metal lower alkyl alcoholates, etc. are preferably used. Specific examples of these compounds are ethylene oxide, propylene oxide, cyclohexene oxide, sodium hydroxide, potassium hydroxide, sodium t-butylate, etc. In view of economy, ethylene oxide and sodium hydroxide are the most preferable.

The reaction in the process of the present invention may proceed in the presence or absence of any solvent at an elevated temperature under an elevated pressure. When any solvent is present, an inert solvent (e.g. alkane, halogenated alkane, benzene or its derivatives, ethers, water) is preferably used. Methylene chloride is the most preferred.

The reaction temperature is preferably not higher than 250° C. and more preferably between 100° C. and 250° C. Generally, the reaction pressure may not be higher than 50 kg/cm$^2$.

After the reaction is completed, low boiling fractions (e.g. halomethane, alkylene oxide, cyclopentadiene, solvent, etc.) are first separated, and then fluorobenzene is recovered from the reaction mixture by distillation. The separated low boiling fractions may be recycled.

Still, the use of cyclopentene in place of cyclopentadiene or its dimer in the above process affords 6-fluoro-6-halogenobicyclo[3.1]hexane. The thus obtained 6-fluoro-6-halogenobicyclo[3.1]hexane is a mixture of the Endo-X form and the Exo-X form of the formulae:

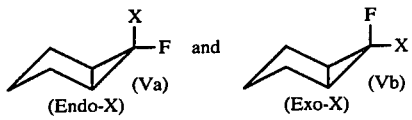

By heating the mixture, the Endo-X form compound is converted into 2-fluoro-1,3-cyclohexadiene while the Exo-X form compound is unchanged.

The present invention will be hereinafter explained further in detail by the following Examples, wherein yield is based on charged halomethane.

EXAMPLE 1

Into an autoclave having an internal volume of 40 ml, cyclopentadiene (9.2 g, 0.139 mol), dichlorofluoromethane (4.5 g, 0.0437 mol), ethylene oxide (5.3 g, 0.121 mol) and $(C_2H_5)_4N^+Br^-$ (0.1 g, $4.8 \times 10^{-4}$ mol) were charged and heated at 160° C. for three hours. After the reaction was completed, the reaction mixture was taken out from the autoclave and distilled to give low boiling fractions (dichlorofluoromethane, ethylene oxide and cyclopentadiene) and then monofluorobenzene (1.92 g, 0.02 mol). Yield: 46%.

EXAMPLES 2 to 9

In the same manner as in Example 1 but the reaction conditions being as shown in Table 1, the fluorobenzene was prepared. The results are as shown in Table 1.

EXAMPLES 12 and 13

In the same manner as in Example 9 but using dibromofluoromethane (Example 12) and difluorochloromethane (Example 13) in place of dichlorofluoromethane, 3.15 g (0.328 mol) and 3.06 g (0.0319 mol) of monofluorobenzene was obtained respectively. Yields: 75% (Example 12) and 73% (Example 13).

EXAMPLE 14

Into a 100 ml reactor equipped with a condenser cooled with dry ice, methylene chloride (25 ml), cyclopentadiene (10 g, 0.15 mol), dichlorofluoromethane (15 g, 0.15 mol) and $(C_2H_5)_3N^+C_6H_4CH_2Cl^-$ (1 g, $4.6 \times 10^{-3}$ mol) were charged, and a 50% aqueous solution of sodium hydroxide (20 ml) was dropwise added over about thirty minutes with vigorous stirring on an ice bath. After addition of sodium hydroxide was finished, stirring was continued for one hour on the ice bath. Thereafter, the reaction mixture was neutralized by hydrochloric acid. An organic layer was separated, dried on anhydrous sodium sulfate and then distilled to give monochlorobenzene (0.9 g). Yield: 6%.

EXAMPLE 15

Into a 100 ml reactor equipped with a condenser cooled with dry ice, methylene chloride (30 ml), cyclopentene (5.1 g, 0.075 mol), dichlorofluoromethane (15.5 g, 0.15 mol) and $(C_2H_5)_3N^+C_6H_4CH_2Cl^-$ (500 mg, $2.3 \times 10^{-3}$ mol) were charged, and a 50% aqueous solution of sodium hydroxide (20 ml) was dropwise added over about fifteen minutes with vigorous stirring on an ice bath. After addition of sodium hydroxide was finished, stirring was continued for one hour on the ice bath. Thereafter, the reaction mixture was neutralized with hydrochloric acid. An organic layer was separated and dried on anhydrous sodium sulfate. Then, the solvent was evaporated off. The residue was distilled under reduced pressure to give 6-fluoro-6-chlorobicyclo[3.1.0]-hexane (2.56 g, 0.019 mol). Yield: 25%. B.P.

TABLE 1

| | Example | | 2 | 3 | 4 | 5 | 6 | 7 | 8 | 9 |
|---|---|---|---|---|---|---|---|---|---|---|
| Reaction | Cyclopentadiene | g (mol) | 9.2 | | | | | | | |
| | | | (0.139) | ← | ← | ← | ← | ← | ← | ← |
| Conditions | Dichlorofluoromethane | g (mol) | 5.0 | | | | | | 5.6 | |
| | | | (0.0485) | ← | ← | ← | ← | ← | (0.0544) | ← |
| | Ethylene oxide | g (mol) | 7.0 | | | | | | | |
| | | | (0.159) | ← | ← | ← | ← | ← | ← | ← |
| | $(C_2H_5)_4N^+Br^-$ | g | 0.10 | 0.4 | | | | | | |
| | $(C_8H_{17})_3N^+CH_3Cl^-$ | g | | | 0.2 | 0.2 | ← | | | |
| | $(C_2H_5)_3N^+C_6H_4CH_2Cl^-$ | g | | | | | | 0.2 | | |
| | $(C_4H_9)_4N^+Br^-$ | g | | | | | | | 0.2 | ← |
| | Temperature | (°C.) | 170 | ← | ← | 200 | ← | 145–150 | 175 | 180 |
| | Time | (hr) | 3.0 | ← | ← | ← | 5.0 | 3.5 | 4.0 | 8.0 |
| | Monofluorobenzene | g (mol) | 1.83 | 0.94 | 1.23 | 1.19 | 1.89 | 1.60 | 3.20 | 4.13 |
| | | | (0.019) | (0.0098) | (0.0134) | (0.0124) | (0.0197) | (0.0167) | (0.0333) | (0.0430) |
| | Yield | % | 39 | 20 | 28 | 26 | 41 | 34 | 61 | 79 |

EXAMPLE 10

In the same manner as in Example 9 but using propylene oxide in place of ethylene oxide, monofluorobenzene (4.08 g, 0.0408 mol) was prepared. Yield: 75%.

EXAMPLE 11

In the same manner as in Example 1 but using methylene chloride (25 ml) as a solvent, monofluorobenzene (3.27 g, 0.0341 mol) was prepared. Yield: 78%.

50° C./40 mmHg. NMR spectrum showed that the obtained product contained the Endo-X form and the Exo-X form in a molar ratio of 7:3.

The thus obtained product (0.14 g, 0.001 mol) was dissolved in quinoline (0.2 ml) and heated at 50° C. for five hours in a sealed glass tube. The reaction mixture was distilled by a per se conventional method to give 2-fluoro-1,3-cyclohexadiene (0.049 g, 0.0005 mol). Yield: 50%.

What is claimed is:

1. A process for preparing monofluorobenzene which comprises reacting cyclopentadiene or its dimer of the formula:

with fluorohalomethane of the formula:

CHFX$_2$ wherein Xs are, same or different, halogen atoms in the presence of a phase transfer catalyst and an acid acceptor at a temperature of from 0° C. to 250° C.

2. The process according to claim 1 wherein the phase transfer catalyst is a quarternary ammonium compound of the formula:

[R$_4$N$^+$]Y$^-$ wherein Rs are, same or different, alkyl groups or aryl groups; Y is an anion selected from the group consisting of halide ion, hydroxide ion, hydrogensulphate ion, hydrogencarbonate ion, dihydrogen phosphate ion and nitrate ion.

3. The process according to claim 1 wherein the acid acceptor is selected from the group consisting of alkylene oxides, alkali metal hydroxides and alkali metal alcoholates.

4. The process according to claim 1 wherein the reaction temperature is a temperature of from 100° C. to 250° C.

* * * * *